United States Patent
Miyajima et al.

(10) Patent No.: US 10,803,564 B2
(45) Date of Patent: Oct. 13, 2020

(54) IMAGE PROCESSING APPARATUS, PROGRAM, AND RADIATION IMAGING APPARATUS

(71) Applicant: Shimadzu Corporation, Kyoto (JP)

(72) Inventors: Takahiro Miyajima, Kyoto (JP); Junya Yamamoto, Kyoto (JP); Kazuyoshi Nishino, Kyoto (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 155 days.

(21) Appl. No.: 16/104,518

(22) Filed: Aug. 17, 2018

(65) Prior Publication Data

US 2020/0058108 A1   Feb. 20, 2020

(51) Int. Cl.
| | |
|---|---|
| G06T 7/66 | (2017.01) |
| G06T 3/60 | (2006.01) |
| G06T 5/00 | (2006.01) |
| G06T 7/00 | (2017.01) |
| G06T 7/77 | (2017.01) |
| A61B 6/00 | (2006.01) |

(52) U.S. Cl.
CPC ............... *G06T 5/008* (2013.01); *A61B 6/50* (2013.01); *A61B 6/5217* (2013.01); *A61B 6/5258* (2013.01); *G06T 3/60* (2013.01); *G06T 7/0012* (2013.01); *G06T 7/66* (2017.01); *G06T 7/77* (2017.01); *G06T 2207/10116* (2013.01); *G06T 2207/20192* (2013.01); *G06T 2207/30061* (2013.01)

(58) Field of Classification Search
None
See application file for complete search history.

(56) References Cited

U.S. PATENT DOCUMENTS

| | | | | |
|---|---|---|---|---|
| 6,282,307 B1* | 8/2001 | Armato, III | ............. | G06K 9/38 382/128 |
| 6,724,925 B2* | 4/2004 | Armato, III | ............. | G06K 9/38 382/132 |
| 9,129,390 B2* | 9/2015 | Dewaele | ................. | G06T 7/168 |
| 2002/0021829 A1* | 2/2002 | Doi | ...................... | G06K 9/6203 382/131 |

(Continued)

FOREIGN PATENT DOCUMENTS

JP    2007-300966 A    11/2007

*Primary Examiner* — Tahmina N Ansari
(74) *Attorney, Agent, or Firm* — Muir Patent Law, PLLC

(57) ABSTRACT

Provided is an image processing apparatus capable of assuredly finding a lung field that appears in an image even if a subject image appears in a radiation image in a rotated manner and assuredly performing a contrast adjustment with excellent visibility for the lung field. The image processing apparatus is provided with a sideways determination means 13 configured to determine that the subject image is turned sideways in the original image P0 when a minimum point P of a profile generated by summing or averaging pixel values belonging to each pixel column of the original image P0 for each pixel column is away from the center position of the subject image. The original image P0 determined as being turned sideways by the sideways determination portion 13 is rotated by the image rotation portion 16 and used for searching of the lung field.

7 Claims, 17 Drawing Sheets

(56) References Cited

U.S. PATENT DOCUMENTS

2011/0305381 A1* 12/2011 Ohno .................... A61B 6/5211
  382/132
2020/0013147 A1* 1/2020 Miyajima ................. G06T 7/30
2020/0058108 A1* 2/2020 Miyajima ................. G06T 7/66

* cited by examiner

↓ Profile generation processing

Profile generation processing

Position

Light area  Right area              Light area

IMAGE PROCESSING APPARATUS, PROGRAM, AND RADIATION IMAGING APPARATUS

TECHNICAL FIELD

The present invention relates to an image processing apparatus, a program, and a radiation imaging apparatus capable of improving visibility of a part of a radiation image.

BACKGROUND ART

FIG. 25 shows a radiation image captured by a radiation imaging apparatus. In order to observe a lung field of a subject appeared in such a radiation image, it is necessary to perform image processing to adjust the contrast of the lung field to improve the visibility of the lung field.

In the radiation image, various portions of a subject, such as a bony part, other than a lung field, are appeared. The bony part of the subject darkly appears in the radiation image because the body part is less likely to allow transmission of radiation. Furthermore, the portion outside the contour of the subject appeared in the radiation image is a portion where the subject does not appear but the air appears. The portion where the subject does not appear brightly appears in the radiation image because there is nothing to transmit radiation. In the radiation image, the lung field is brighter than the bony part of the object but darker than the portion outside the contour of the subject which is the portion where the air appears.

The lung field of the radiation image totally looks to be filled with a gray color with poor contrasting density. This is because the pixels located in the lung field appeared in the radiation image have similar pixel values.

When the contrast adjustment is executed for the entire radiation image for the purpose of increasing the visibility of the lung field, the contrast adjustment is also executed for the portions of the radiation image in which the bony parts and the air appeared. Although such a contrast adjustment may increase the visibility of the radiation image as a whole, as far as the lung field is concerned, there is not so much improvement in visibility. The lung field after the contrast adjustment is still in a poor total contrast density state. This is because of the following reasons. That is, in the case of expressing the contrasting density of the lung field, low pixel values are used to express bony parts of a subject, and high pixel values are used to express the portion where the air appears. Therefore, the lung field should be expressed with the remaining moderate pixel values.

Therefore, a method of making a contrast adjustment only on a lung field in a radiation image has been conventionally conceived. According to this method, since the lung field can be expressed with more various color tones, the visibility of the lung field is assuredly increased. In this method, trimming is performed to extract a lung field in a radiation image, and a contrast adjustment is executed on the trimmed image in which the lung field largely appears. In the trimmed image, dark bony parts of the subject and bright portions where the air appears are excluded, so the trimmed image is not affected by these portions.

FIG. 26 shows lung field search processing for finding a lung field to be subjected to a contrast adjustment from a radiation image. In this lung field search processing, based on the distribution of pixel values of the subject image, a part in which the lung field appears is searched from the radiation image and an area surrounding the part is specified. From the viewpoint of performing a contrast adjustment only on a lung field, it is desirable that the area be as narrow as possible while including the entire lung field. The area searched by the lung field search processing becomes a trimmed image to be subjected to a contrast adjustment (see, for example, Patent Document 1 as an example of the image processing).

PRIOR ART

Patent Document

Patent Document 1: Japanese Unexamined Patent Application Publication No. 2007-300966

SUMMARY OF THE INVENTION

Problems to be Solved by the Invention

However, a contrast adjustment of a conventional configuration does not take into consideration a direction in which a subject appears.

In a conventional lung field search processing, it is premised that the image is captured with the upper portion of the subject arranged in a direction toward the upper side of the image. In such an image, the subject's right lung appears on the right side of the image and the subject's left lung appears on the left side. The areas below the right lung and the left lung in the image are not lung fields. Conventional lung field search processing is configured to search lung fields appeared described above from the image.

FIG. 27 shows a state in which conventional lung field search processing is applied to a radiation image in which a subject is appeared sideways. In this radiation image, since the subject image appears sideways, the right lung image that should appear on the right side of the image appears at the upper portion of the image, and the left lung image that should appear on the left side of the image appears at the lower portion of the image. Such a radiation image is often captured when a child's subject is imaged, but might be captured in normal imaging.

When lung field search processing is applied to a radiation image as shown in FIG. 27, a phenomenon that the right lung image appearing at the upper portion of the image is falsely recognized as lung fields may occur. On the lower side of the right lung image, there should be originally a left lung image which should originally be included in the lung field. However, in the lung field search processing, it is only possible to recognize that a bright portion forming a right lung image at the upper portion of the image is a lung field and that there exists no lung field below the bright portion. Therefore, according to a conventional configuration, a contrast adjustment is performed only on the right lung image. As described above, conventional image processing has a problem that a correct contrast adjustment cannot be performed depending on a radiation image.

The present invention has been made in view of the aforementioned circumstances, and an object of the present invention is to provide an image processing apparatus capable of assuredly finding a lung field that appears in an image even if a subject image appears in a radiation image in a rotated manner and assuredly performing a contrast adjustment with excellent visibility for the lung field.

Means for Solving the Problems

In order to solve the aforementioned problems, the present invention has the following configuration.

That is, the image processing apparatus according to the present invention includes: in an image processing apparatus configured to apply a luminance adjustment to a lung field corresponding portion of a radiation image in which a subject image appears, profile generation means configured to generate a profile by summing or averaging pixel values belonging to each pixel column of the radiation image for each pixel column;

center position calculation means configured to calculate a center position which is a position of a center of the subject image which appears in the radiation image;

sideways determination means configured to determine that the subject image is turned sideways in the radiation image when a minimum position which is a position where a value of a profile is minimum is away from the center position of the subject image and determine that the subject image appears vertically in the radiation image when the minimum position of the profile is in a vicinity of the center position; and lung field search processing means configured to search the lung field which appears in the radiation image based on a determination result.

[Functions and Effects]

According to the present invention, it is possible to provide an image processing apparatus capable of assuredly finding a lung field that appears in an image even if a subject image appears in a radiation image in a rotated manner and assuredly performing a contrast adjustment with excellent visibility for the lung field. That is, the image processing apparatus is provided with a sideways determination means configured to determine that the subject image is turned sideways in the radiation image when a minimum position of a profile generated by summing or averaging pixel values belonging to each pixel column of the radiation image for each pixel column is away from the center position of the subject image. Since the lung field search can be performed in a state in which how the lung field appears in the radiation image is recognized by the sideways determination means, the contrast adjustment excellent in visibility can be assuredly performed for the lung field.

Also, in the above-described image processing apparatus, it is more preferable that the image processing apparatus further include image rotation means configured to perform rotation processing for rotating the radiation image with respect to the radiation image determined as being turned sideways by the sideways determination means and that the lung field search processing means perform searching of the lung field for the radiation image after the rotation processing.

[Functions and Effects]

The above-described configuration explains a more specific configuration of the present invention. The radiation image determined as being turned sideways by the sideways determination means is rotated by the image rotation means and used for searching of the lung field. Therefore, according to the present invention, even if the subject image appears in a rotated manner in the radiation image, the lung field search can be performed with the subject image corrected to the correct orientation.

Also, in the above-described image processing apparatus, it is more preferable that the lung field search processing means perform searching of the lung field for the radiation image determined by the sideways determination means that the subject image appears vertically in the radiation image.

[Functions and Effects]

The above-described configuration explains a more specific configuration of the present invention. That is, according to the apparatus of the present invention, when the subject image appears vertically in the radiation image, the lung field search processing is executed without rotating the image.

Further, in the aforementioned image processing apparatus, it is more preferable that the image processing apparatus further include contour extraction means configured to generate a contour extracted image by extracting a contour of the image appeared in the radiation image determined as being turned sideways by the sideways determination means and left/right determination means configured to determine that an area on a side with larger variations corresponds to an upper portion of the subject image by comparing a variation in pixel values in an area on a right side of the contour extracted image and a variation in pixel values in an area on a left side of the contour extracted image, and the image rotation means rotate the radiation image so that the upper portion of the subject image faces an upper side of the radiation image depending on a determination result of the left/right determination means.

[Functions and Effects]

The above-described configuration explains a more specific configuration of the present invention. By providing the left/right determination means configured to determine which direction the subject image is turned sideways with respect to the radiation image determined to be turned sideways by the sideways determination means, it is possible to rotate the radiation image so that the upper portion of the subject image assuredly faces the upper side of the radiation image.

Further, in the aforementioned image processing apparatus, it is more preferable that the image processing apparatus further include contour extraction means configured to generate a contour extracted image by extracting a contour of the image appeared in the radiation image determined such that the subject image appears vertically in the radiation image by the sideways determination means and up/down determination means configured to determine that an area on a side with larger variations corresponds to an upper portion of the subject image by comparing a variation in pixel values in an area on an upper side of the contour extracted image and a variation in pixel values in an area on a lower side of the contour extracted image, and the image rotation means rotate the radiation image so that the upper portion of the subject image positioned below the radiation image faces the upper side of the radiation image.

[Function and Effects]

The above-described configuration explains a more specific configuration of the present invention. By providing the up/down determination means configured to determine whether the subject is turned upside-down with respect to the radiation image which is determined by the sideways determination means such that the subject image appears vertically, it is possible to rotate the radiation image so that the upper portion of the subject image assuredly faces the upper side of the radiation image.

Effects of the Invention

According to the present invention, it is possible to provide an image processing apparatus capable of assuredly finding a lung field that appears in an image even if a subject image appears in a radiation image in a rotated manner and assuredly performing a contrast adjustment with excellent visibility for the lung field. That is, the image processing apparatus is provided with a sideways determination means configured to determine that the subject image is turned sideways in the radiation image when a minimum position of a profile generated by summing or averaging pixel values belonging to each pixel column of the radiation image for each pixel column is away from the center position of the subject image. The radiation image determined as being turned sideways by the sideways determination means is rotated by the image rotation means and used for searching of the lung field.

EXAMPLE 1

EMBODIMENTS FOR CARRYING OUT THE INVENTION

Figure 1:
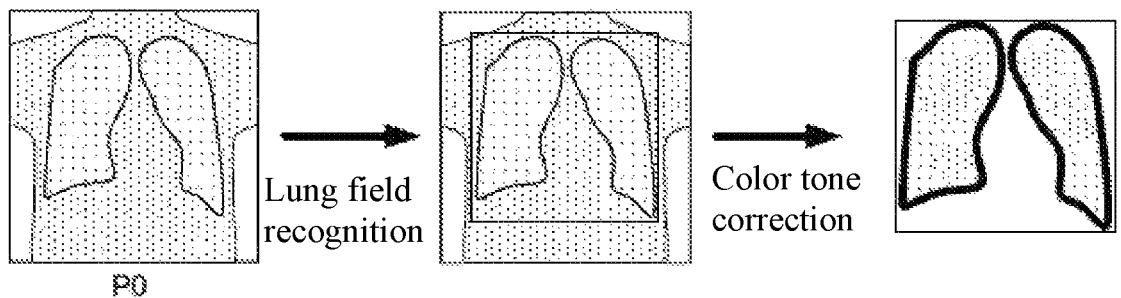
FIG. 1 is a schematic diagram roughly explaining an operation of an image processing apparatus according to Example 1.

Next, some examples according to the present invention will be described. As shown in FIG. 1, in the image processing apparatus 1 according to the present invention, when a chest X-ray image (original image P0) of a subject imaged by an X-ray imaging apparatus is input, it is configured to recognize where the lung field appears in the original image P0, set the lung field area, and output the image in which a color tone correction is performed to the set lung field area. The image processing apparatus according to the present invention is configured to apply a luminance adjustment to the portion corresponding to the lung field in the original image P0 in which the subject image appears.

Figure 2:
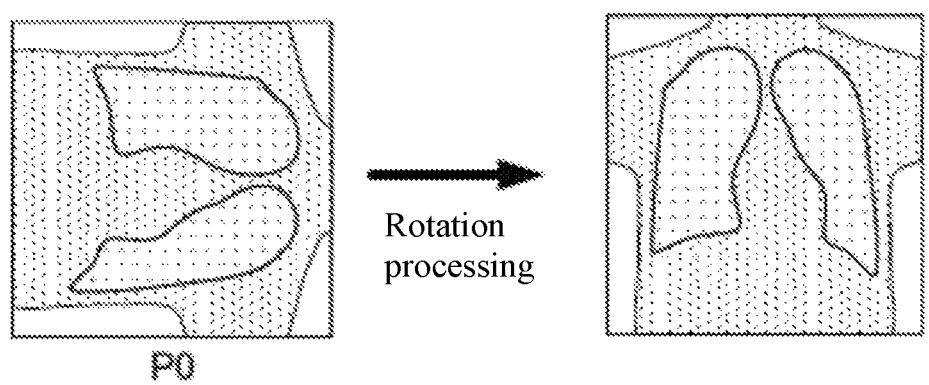
FIG. 2 is a schematic diagram explaining operational features of the image processing apparatus according to Example 1.

In addition to such a conventional function, in the present invention, as shown in FIG. 2, when an original image P0 in which a subject image is turned sideways is input, it is configured to recognize the turning sideways of the subject image and rotate the original image P0 so that the direction of the subject image matches the orientation of the original image P0. The rotation of this original image P0 is performed before recognition of the lung field area and the color tone correction. Therefore, when the original image P0 in which the object appears in a turned sideways manner is input in the apparatus according to the present invention, the original image P0 is rotated by 90°. After the turning sideways of the image is corrected, the setting of the lung field area and the color tone correction will be performed. In the present invention, the function of rotating this original image P0 is most characteristic.

Figure 3:
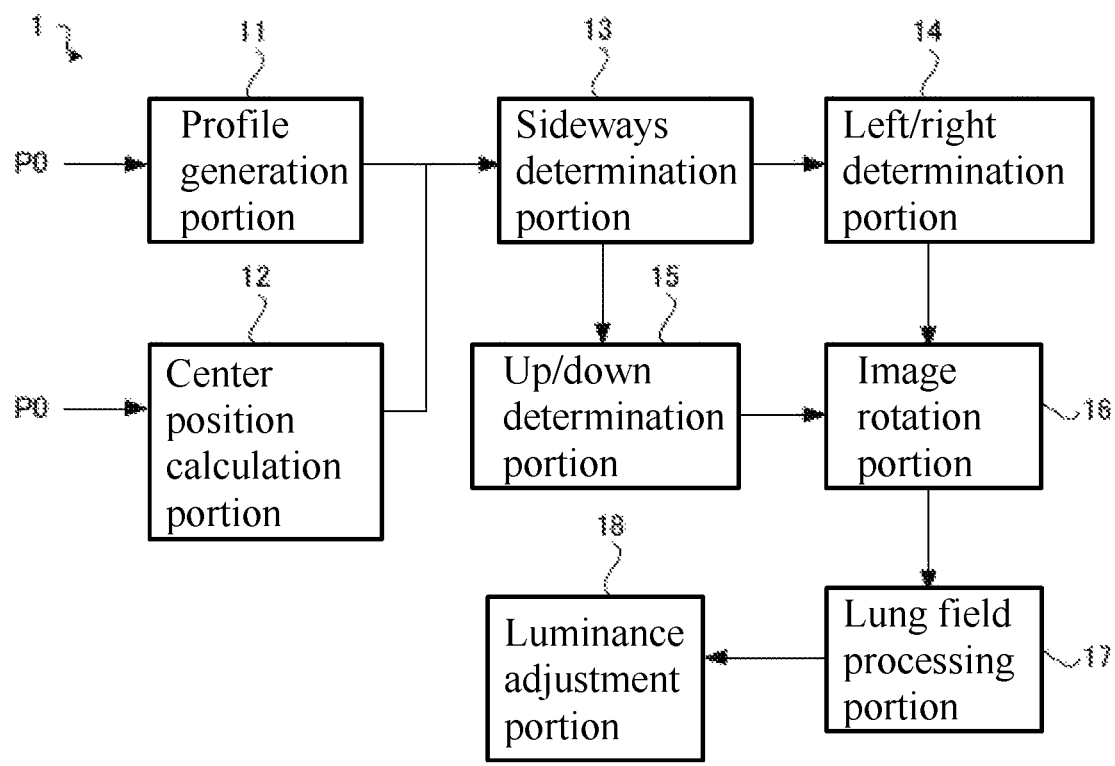
FIG. 3 is a functional block diagram explaining a configuration of the image processing apparatus according to Example 1.

FIG. 3 is a functional block diagram showing the entire image processing performed by the image processing apparatus 1. According to FIG. 3, the profile generation portion 11, the center position calculation portion 12, the sideways determination portion 13, the left/right determination portion 14, and the image rotation portion 16 perform the operation of rotating the original image P0 by 90° described with reference to FIG. 2. This operation will not be performed on the original image P0 in which the subject appears vertically as described in FIG. 1.

The up/down determination portion 15 is a configuration related to a case in which an operation of rotating an original image P0 by 180° is performed with respect to the original image P0 in which a subject image appears upside-down among original images P0 in which the subject appears vertically. The lung field search processing portion 17 is configured to search the position of the lung field in the subject image on the original image P0 to determine the lung field area. The luminance adjustment portion 18 is configured to perform a contrast adjustment (color tone correction) for the lung field area.

Note that the profile generation portion 11 corresponds to the profile generation means of the present invention and the center position calculation portion 12 corresponds to the center position calculation means of the present invention. The sideways determination portion 13 corresponds to the sideways determination means of the present invention and the image rotation portion 16 corresponds to the image rotation means of the present invention. The lung field search processing portion 17 corresponds to the lung field search processing means of the present invention.

The apparatus according to the present invention is characterized in a configuration in which it is determined whether or not the subject image appears vertically or horizontally in the original image P0 and also determined whether the original image P0 should be rotated according to the determination result. As to how to determine presence or absence of turning sideways of the subject image, since each portion of the profile generation portion 11, the center position calculation portion 12, and the sideways determination portion 13 is related, these will be explained step by step.

<Operation of Profile Generation Portion 11>

Figure 4:
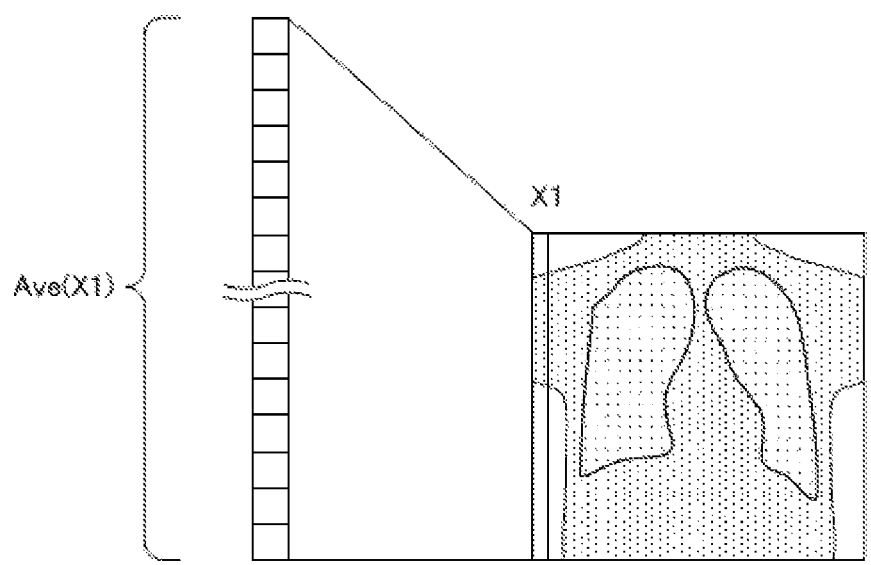
FIG. 4 is a schematic diagram explaining profile generation processing according to Example 1.
Figure 5:
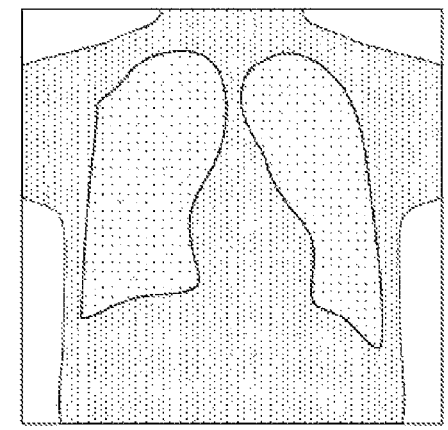
FIG. 5 is a schematic diagram explaining the profile generation processing according to Example 1.
Figure 5:
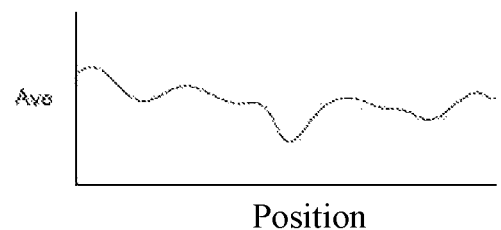

FIG. 4 shows the operation of the profile generation portion 11. The profile generation portion 11 calculates an average value by averaging the pixel value of each pixel belonging to a pixel column of interest in which pixels each having a width of one pixel are arranged in a vertical direction in the original image P0 configured by vertically and horizontally arranging pixels. In the explanation of FIG. 4, the average value Ave (X1) is calculated for the pixel column related to the left end position X1 in the original image P0. The profile generation portion 11 repeats the calculation of the average value Ave while moving the pixel column of interest in a lateral direction by one pixel to the right and calculates up to the pixel column of the right end position in the original image P0. Then, as shown in FIG. 5, the profile generation portion 11 generates a profile in which the average value Ave and the position of the pixel column of interest related to the average value Ave are related. Therefore, this profile becomes a profile extended in the lateral direction for the original image P0. In this way, the profile generation portion 11 generates the profile by summing or averaging the pixel values belonging to each pixel column of the original image P0 for each pixel column.

In the above description, the profile generation portion 11 sequentially calculates the average value Ave from the left end of the original image P0 to the right end thereof, but the sequence of calculation need not be this procedure. This situation is the same in FIG. 6 and FIG. 7 which will be described later.

Figure 6:
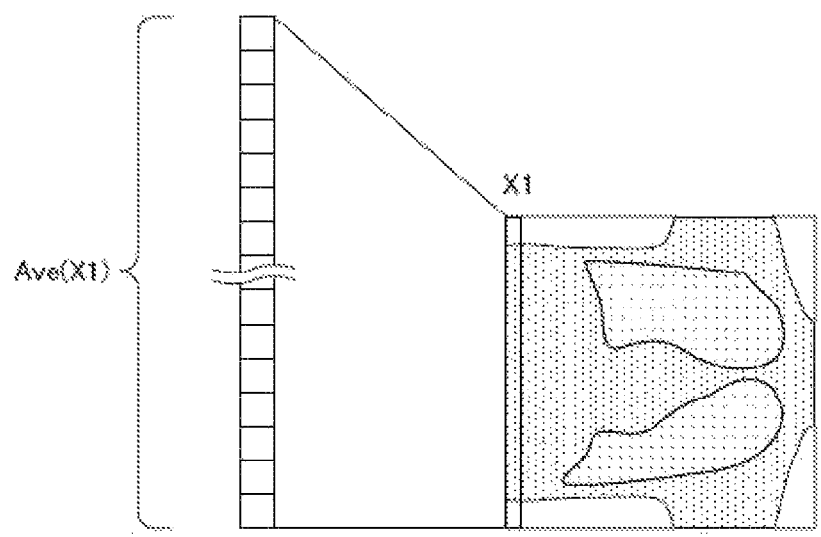
FIG. 6 is a schematic diagram explaining the profile generation processing according to Example 1.
Figure 7:
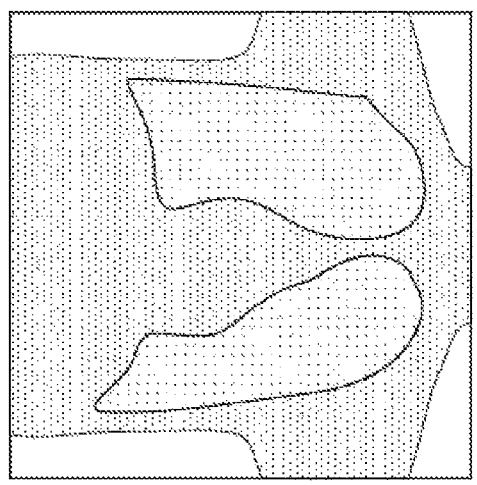
FIG. 7 is a schematic diagram explaining the profile generation processing according to Example 1.
Figure 7:
Figure 7:
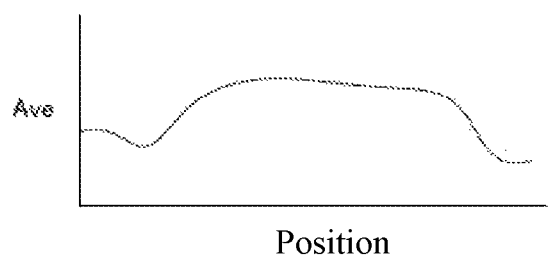

In the explanation of FIG. 4 and FIG. 5, the subject image appears vertically in original image P0. Note that, in the apparatus of the present invention, the original image P0 in which the subject image is turned sideways as described in FIG. 2 may sometimes be input. FIG. 6 shows how the profile generation portion 11 generates a profile for the original image P0 in which the subject image is turned sideways. Since the original image P0 has been defined as to which side is the upper side, the profile generation portion 11 calculates the average value Ave (X1) for the pixel column related to the left end position X1 in the original image P0 while keeping the state in which the subject image is turned sideways, and repeats the calculation of the average Ave while moving the pixel column of interest by one pixel in the lateral direction. Then, a profile as shown in FIG. 7 is generated.

Figure 8:
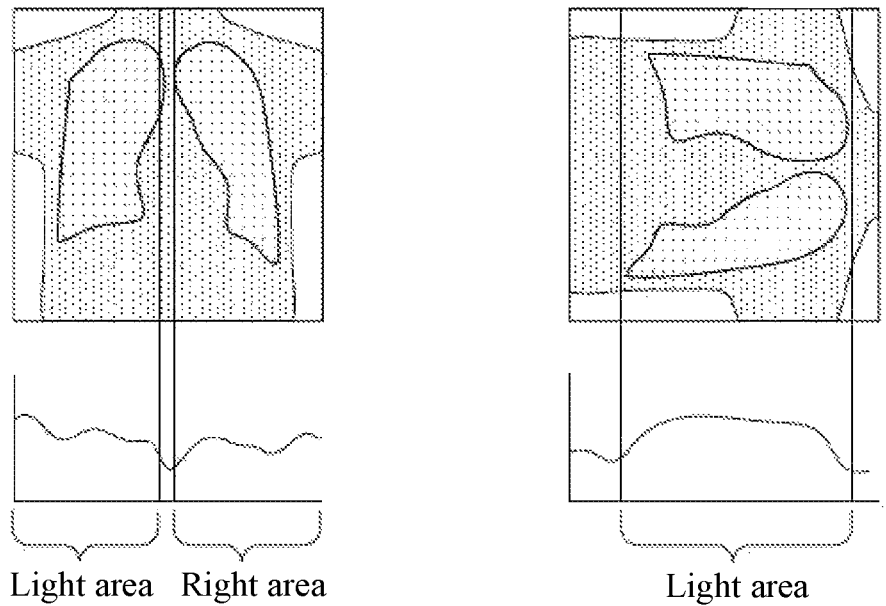
FIG. 8 is a schematic diagram explaining features of the profile according to Example 1.

FIG. 8 explains how the profile varies depending on whether the subject image is turned sideways. The left side of FIG. 8 shows the case in which the vertically arranged subject appears in the original image P0. The profile in this case shows that the central part is dented. This dent is in a position sandwiched between the light area derived from the bright left lung on the original image P0 and the light area derived from the bright right lung, and the value of this portion is the average value obtained by averaging the pixel values of the pixels located in the dark spine.

On the other hand, the right side of FIG. 8 shows the case in which the subject turned sideways appears in the original image P0. In the profile in this case, no dent appears in the center, and only a single wide light area appears at the center. The influence of the pixel value of the pixels located on the dark spine in the original image P0 on the profile is dispersed over the entire profile and is not concentrated on a specific part of the profile. Therefore, the lowest value in the profile at this time is at the end portion where the bright lung field is not located on the original image P0.

Therefore, in cases where the lowest value of the profile appears in the center of the profile, it might be said that the subject arranged vertically appears in the original image P0. For this reason, in cases where the lowest value of the profile appears at the end portion of the profile, it might be said that the subject turned sideways appears in the original image P0. Actually, in the present invention, using this principle, the presence or absence of the turning sideways of the subject in the original image P0 is determined.

Figure 9:
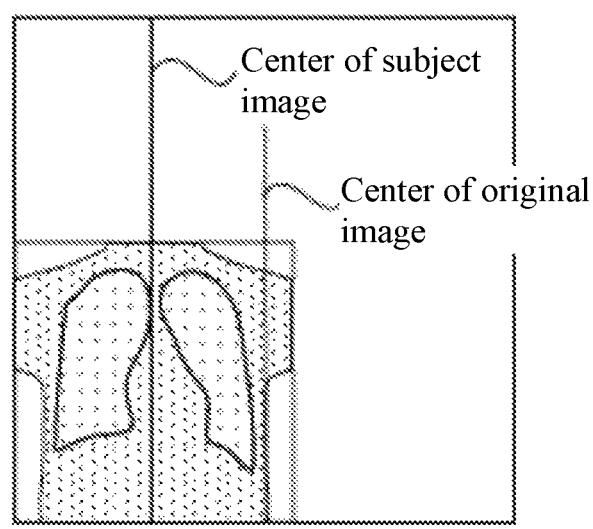
FIG. 9 is a schematic diagram explaining the problem of the profile according to Example 1.

However, false recognition may occur if whether or not the subject image is turned sideways is determined based on only the lowest value position of the profile. FIG. 9 explains the circumstances. In cases where the subject image biasedly appears on the end portion of the original image P0, the center of the subject image and the center of the original image P0 are separated. Since the profile is generated over the entire original image P0, the minimum value of the profile will appear at the end portion of the profile. In such a case, the original image P0 in which the subject image which has not been turned sideways appears will be falsely recognized as being turned sideways, and therefore the image will be rotated. Such a phenomenon is particularly likely to occur on the original image P0 imaging an infant.

In the present invention, in order to prevent such false recognition, the center of the subject image which appears in the original image P0 is calculated. This operation is performed by the center position calculation portion 12.

<Operation of Center Position Calculation Portion 12>

The center position calculation portion 12 is a configuration for calculating the center of the subject image that appears in the original image P0. The center position calculation portion 12 initially applies edge enhancement processing to the original image P0 to generate an edge enhanced image. The edge enhancement processing is executed by applying a differential filter, such as, e.g., a Sobel filter, to the original image P0. When trying to obtain the center of the subject image directly with respect to the original image P0, the result differs depending on the pixel value of the pixel located in the outside area of the subject image. By applying edge enhancement processing, it is possible to emphasize the structural object itself which appears in the original image P0, so that the center of the subject image can be assuredly calculated.

Figure 11:
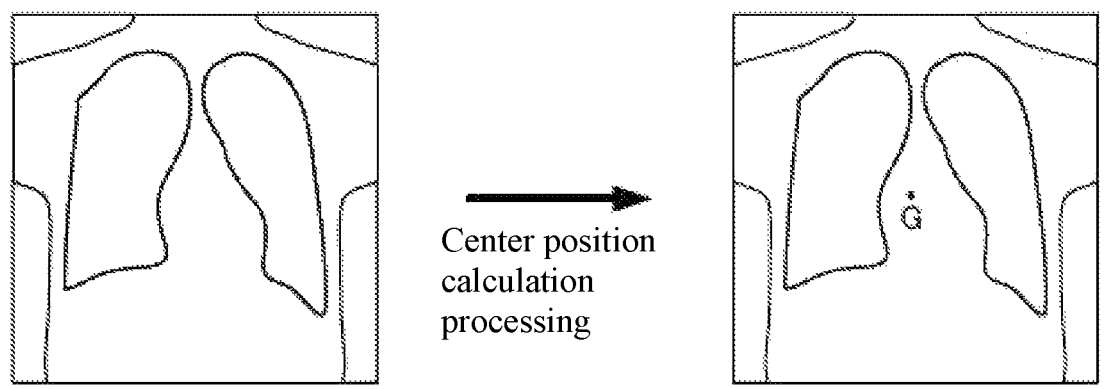
FIG. 11 is a schematic diagram explaining the center position calculation processing according to Example 1.

FIG. 11 shows how the center position calculation portion 12 calculates the center of gravity G of the subject image with respect to the edge enhanced image of the original image P0 in which the subject appears in the vertical direction. The coordinates of the center of gravity G (Gx, Gy) on the edge enhanced image are obtained as follows.

$$Gx = \Sigma I(x) \cdot x / \Sigma I(x)$$

$$Gy = \Sigma I(y) \cdot y / \Sigma I(y)$$

Here, "x" represents the position of the edge enhanced image in the lateral direction, and "I(x)" represents the sum of the pixel values of the pixels of the edge enhanced image at the position "x".

Further, "y" represents the position of the edge enhanced image in the lateral direction, and "I(y)" represents the sum of the pixel values of the pixels of the edge enhanced image at the position "y". Note that in the present invention, since the coordinates of the center of gravity G are used for calculation only in the lateral direction, it is not always necessary to calculate Gy. However, for convenience of explanation, it is assumed that the position of the center of gravity G is obtained.

In FIG. 11, since the edge emphasized image of the subject appears throughout the edge enhanced image, the position of the center of gravity G appears near the center of the image. The position of the center of gravity G indicates the center of the subject image on the original image P0.

Figure 12:
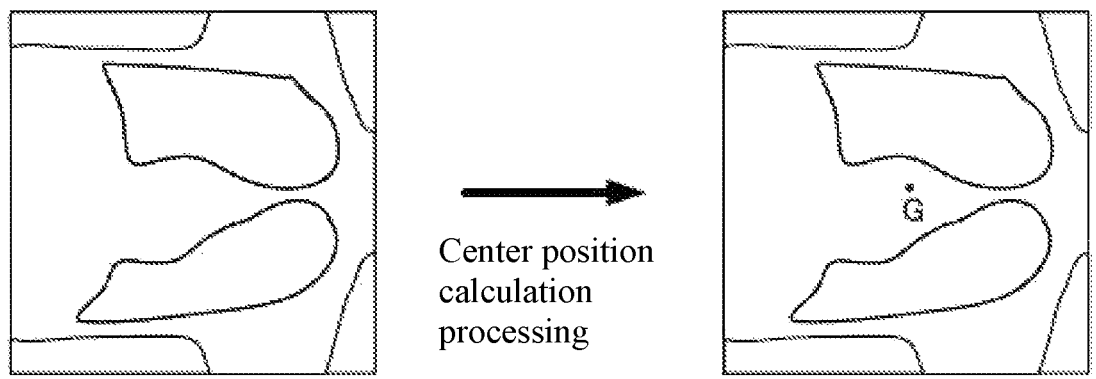
FIG. 12 is a schematic diagram explaining the center position calculation processing according to Example 1.

FIG. 12 shows how the center position calculation portion 12 calculates the center of gravity G of the subject image with respect to the edge enhanced image of the original image P0 in which the subject is turned sideways. In FIG. 12, since the edge emphasized image of the subject appears throughout the edge enhanced image, the position of the center of gravity G appears near the center of the image. This position of the center of gravity G indicates the center of the subject image on the original image P0. In this manner, the center position calculation portion 12 calculates a center position (center of gravity G) which is the center position of the subject image which appears in the original image P0.

Figure 13:
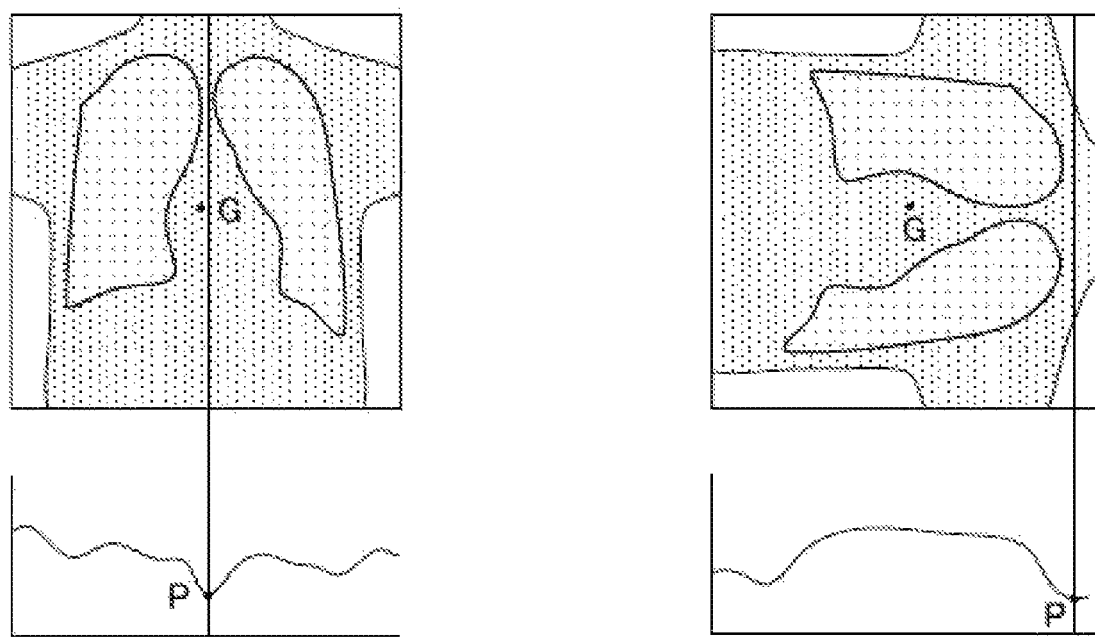
FIG. 13 is a schematic diagram explaining a relationship between the center position and the profile according to Example 1.

FIG. 13 shows the relationship between the center of gravity G and the profile. The left side of FIG. 13 illustrates the positional relationship in the case in which the subject appears in the vertical direction in the original image P0, and the minimum point P in which the profile is minimum is close to the position of the center of gravity G. The right side of FIG. 13 illustrates the positional relationship in the case in which the subject turned sideways appears in the original image P0, and the minimum point P having the minimum profile is away from the position of the center of gravity G. In other words, by examining the positional relationship between the minimum point P and the center of gravity G, it is possible to know whether or not the subject on the original image P0 is turned sideways.

<Operation of Sideways Determination Portion 13>

The sideways determination portion 13 is a configuration for determining the presence or absence of the turning sideways of the subject image based on this principle. To the sideways determination portion 13, the profile of the original image P0 is sent from the profile generation portion 11, and coordinates indicating the position of the center of gravity G are sent from the center position calculation portion 12.

Figure 14:
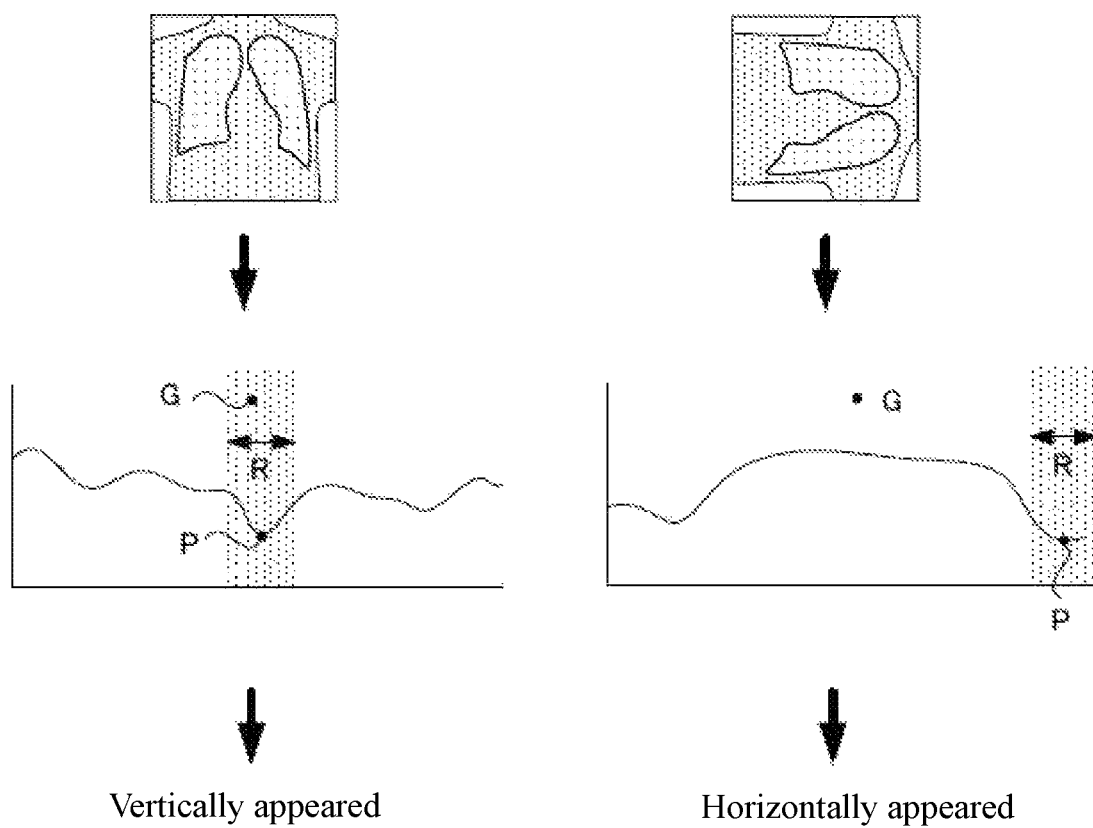
FIG. 14 is a schematic diagram explaining sideways determination processing according to Example 1.

FIG. 14 explains the sideways determination processing executed by the sideways determination portion 13. That is, as shown on the left side of FIG. 14, when the position of the center of gravity G in the lateral direction is within a predetermined range R with reference to the position of the profile minimum point P in the lateral direction as the reference, the sideways determination portion 13 determines that the subject image on the original image P0 is not turned sideways and appears in the vertical direction.

Further, as shown in the right side of FIG. 14, when the position of the center of gravity G in the lateral direction does not belong to the predetermined range R with reference to the position of the profile minimum point P in the lateral direction, the sideways determination portion 13 determines that the subject image on the original image P0 is turned sideways.

In the sideways determination portion 13, the position of the center of gravity G is determined with reference to the minimum point P, but the present invention is not limited to this configuration. The sideways determination may be performed based on whether or not the position of the minimum point P is within a predetermined range with reference to the center of gravity G. In any case, the sideways determination portion 13 determines that the subject image is turned sideways in the original image P0 when the minimum point P, which is the position where the value of the profile is the minimum, is away from the center position of the subject image, and determines that the subject image appears vertically in the original image P0 when the minimum point P of the profile is in the vicinity of the center position.

Figure 15:
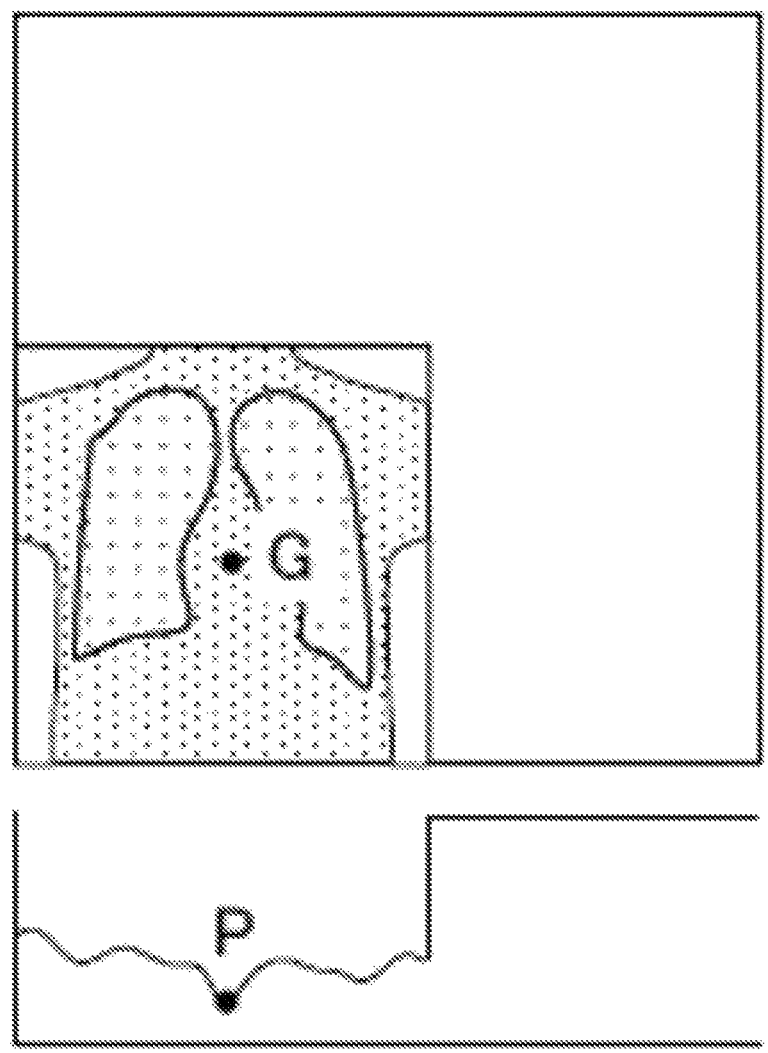
FIG. 15 is a schematic diagram explaining the sideways determination processing according to Example 1.

In this way, by determining the presence or absence of the turning sideways of the subject image by comparing the position of the minimum point P of the profile and the position of the center of gravity G, as shown in FIG. 15, it is possible to make a correct determination even when the subject image appears so as to be shifted toward the end portion on the original image P0. This is because when the subject image appears so as to be shifted toward the end portion on the original image P0, the position of the center of gravity G is also shifted toward the end portion so as to follow the subject image and therefore it can be assuredly grasped whether the minimum point P of the profile is at the center of the subject image or at the end portion.

Figure 16:
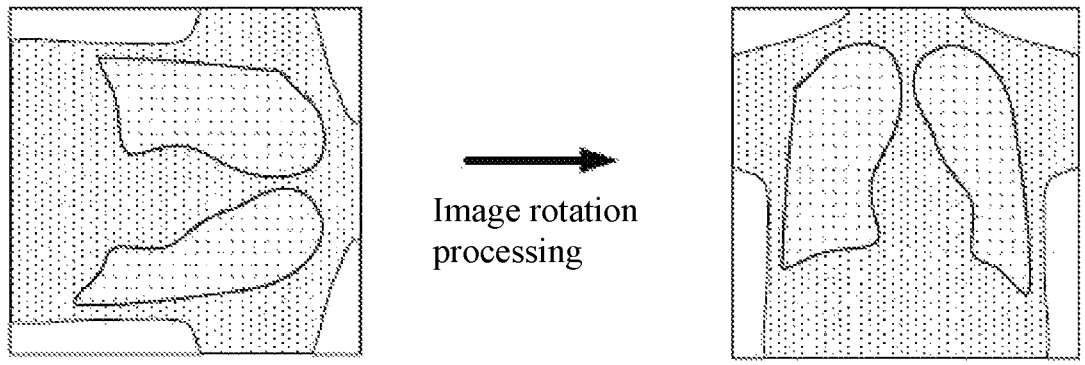
FIG. 16 is a schematic diagram explaining image rotation processing according to Example 1.

When it is determined by the sideways determination portion 13 such that the original image P0 is turned sideways, as shown in FIG. 16, the original image P0 is rotated by 90° by the image rotation processing, so that the orientation of the subject image on the original image P0 is corrected so that the upper portion (head) is positioned on the upper side of the image and the abdomen is positioned on the lower side of the image. The rotation processing of such an image is performed by the image rotation portion 16. The image rotation portion 16 executes rotation processing to rotate the original image P0 with respect to the original image P0 determined as being turned sideways by the sideways determination portion 13.

Figure 17:
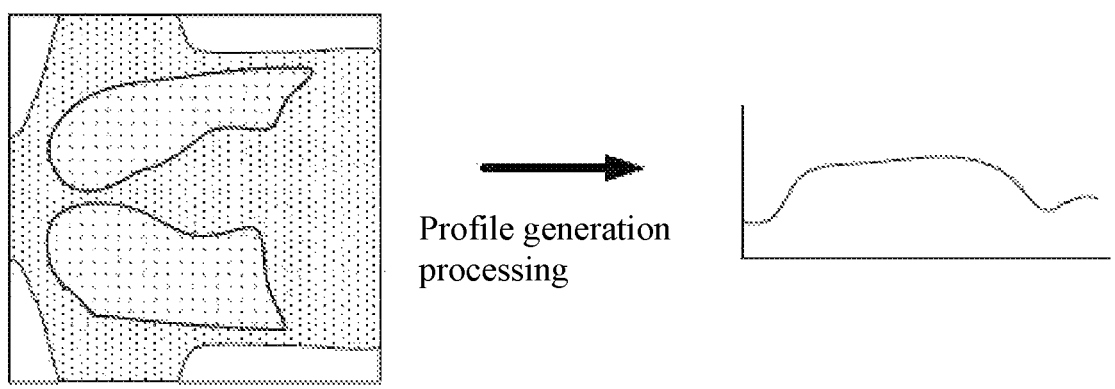
FIG. 17 is a schematic diagram explaining the problem of the profile according to Example 1.

However, with this operation, it cannot be determined which direction the original image P0 should be rotated by 90°. What can be determined by the sideways determination portion 13 is that whether or not the subject image on the original image P0 is turned sideways. It cannot be distinguished whether the upper portion of the subject image is positioned on the upper side of the image by rotating the original image P0 by 90° clockwise, or whether the upper portion of the subject image is positioned on the upper side of the image by rotating the original image P0 by 90° counterclockwise. FIG. 17 explains this situation. FIG. 17 shows an original image P0 in which the subject image is turned sideways leftward, and shows an image in which the subject image shown on the right side of FIG. 8 is oriented oppositely. The profile generated by the profile generation portion 11 based on the original image P0 shown in FIG. 17 is the similar to the profile on the subject image shown on the right side of FIG. 8. Therefore, based on the profile, it is difficult to determine whether the upper side of the image corresponds to the right of the image or the left of the image.

Therefore, the apparatus according to the present invention is provided with a configuration for determining whether the subject image is turned sideways rightward or turned sideways leftward. This determination is performed by the left/right determination portion 14.

<Operation of Left/Right Determination Portion 14>

Figure 10:
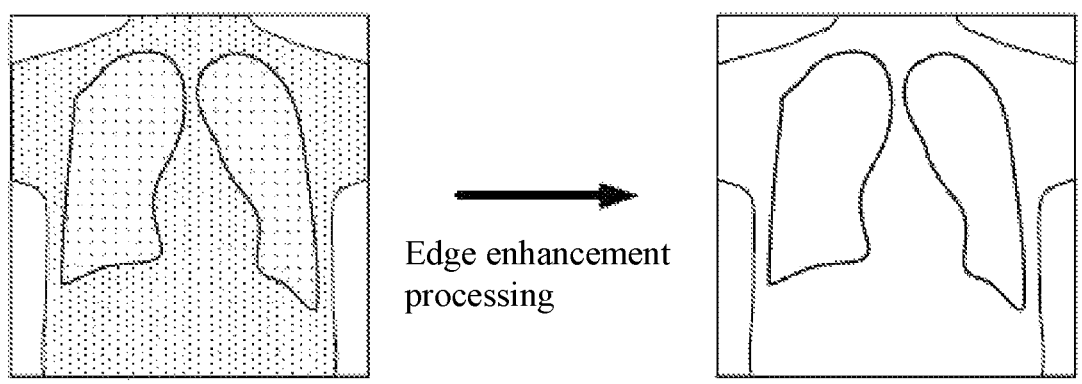
FIG. 10 is a schematic diagram explaining center position calculation processing according to Example 1.
Figure 18:
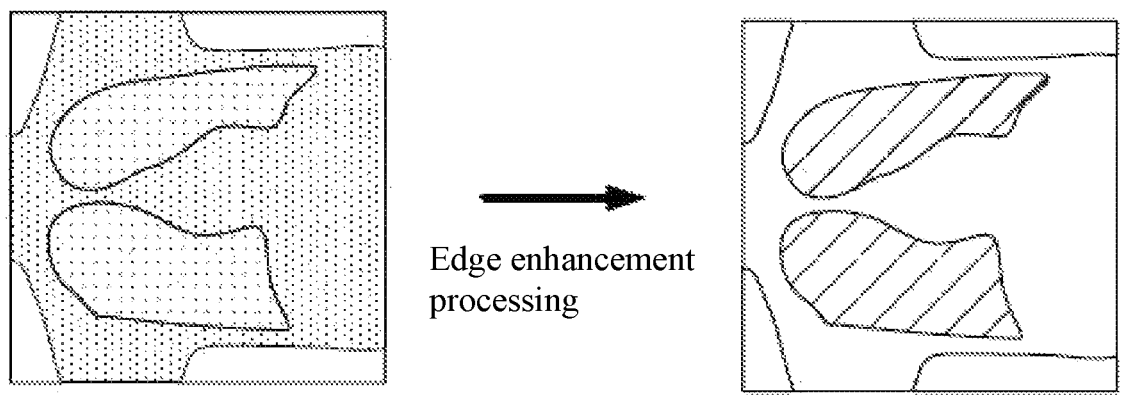
FIG. 18 is a schematic diagram explaining left/right determination processing according to Example 1.

The determination result of the sideways determination portion 13 is sent to the left/right determination portion 14. When it is determined that the original image P0 is turned sideways, as shown in FIG. 18, the left/right determination portion 14 initially performs edge enhancement processing on the original image P0 to generate an edge enhanced image. The edge enhancement processing is performed by applying a filter, such as, e.g., a Laplacian filter, to the original image P0. The edge enhanced image generated at this time will be referred to as a left/right determination image in order to distinguish from the image depicted in FIG. 10.

The left/right determination portion 14 sets two areas on the left/right determination image, i.e., a right area which corresponds to the right half of the image and a left area which corresponds to the left half of the image. That is, the right area and the left area are set by vertically dividing the left/right determination image into two equal parts. Then, the left/right determination portion 14 calculates the standard deviation $\sigma(R)$ of the pixel values of the pixels belonging to the right area and the standard deviation $\sigma(L)$ of the pixel values of the pixels belonging to the left area.

Figure 19:
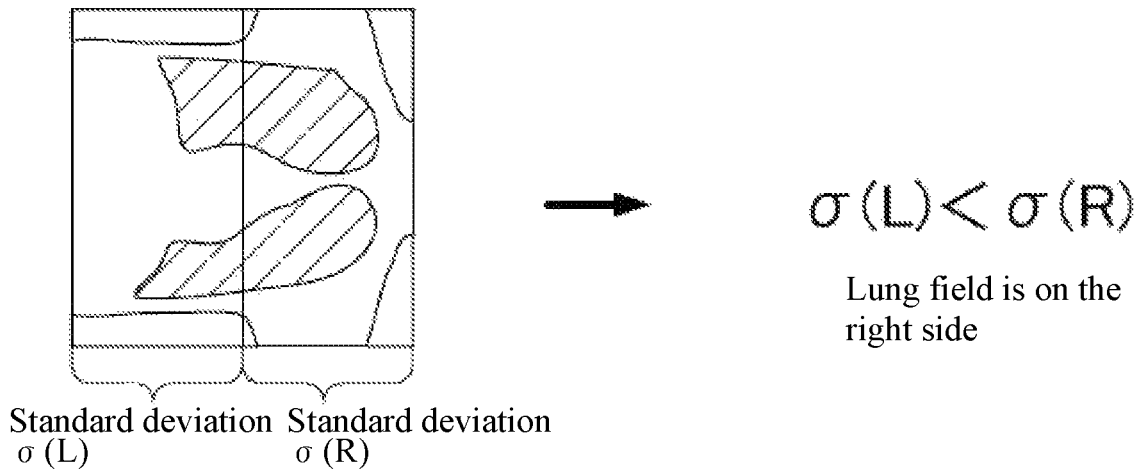
FIG. 19 is a schematic diagram explaining the left/right determination processing according to Example 1.

FIG. 19 shows a left/right determination image according to the original image P0 in which the subject image is turned sideways so that the upper portion (head) is positioned on the right side of the image appears. The standard deviation $\sigma(R)$ calculated from this image is larger than the standard deviation $\sigma(L)$. This is because that the subject's lung field is shifted to the right of the image. A subject's lung is low in density and readily allows passing of X-rays. Lungs are protected by ribs. Ribs are bones, so they are high in density and less likely to allow passing of X-rays. Therefore, the lung field on the original image P0 is an image in which dark portions and bright portions are arranged in a stripe manner. When edge enhancement processing is performed on such original image P0, the variation of the pixel values of the pixels located in the lung field of the obtained left/right determination image becomes large, and becomes smaller in the portion other than the lung field. When the lung field of the subject is shifted to the right side of the image, the standard deviation $\sigma(R)$ showing the variation of pixel values of the pixels belonging to the right area becomes large and the standard deviation $\sigma(L)$ showing the variation of pixel values of the pixels belonging to the left area becomes small. Since the majority of the lung field should be shifted toward the upper portion of the subject image, the right area of the original image P0 corresponds to the upper portion of the subject image. Based on this principle, when the standard deviation $\sigma(R)$ is larger than the standard deviation $\sigma(L)$, the left/right determination portion 14 determines that the subject image is turned sideways on the original image P0 so that the upper portion is on the right side of the image.

Figure 20:
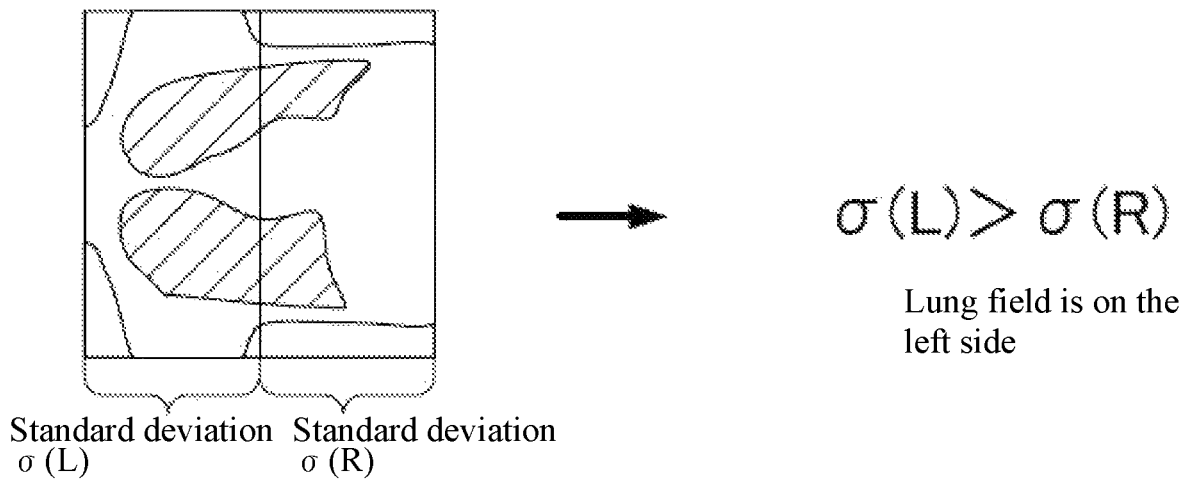
FIG. 20 is a schematic diagram explaining the left/right determination processing according to Example 1.

FIG. 20 shows a left/right determination image according to the original image P0 in which the subject image is turned sideways so that the upper portion is positioned on the right side of the image appears. The standard deviation $\sigma(L)$ calculated from this image is larger than the standard deviation $\sigma(R)$. This is because that the subject's lung field is shifted to the left of the image. Since the majority of the lung field should be shifted toward the upper portion of the subject image, the left area of the original image P0 corresponds to the upper portion of the subject image. Based on this principle, when the standard deviation $\sigma(L)$ is larger than the standard deviation $\sigma(R)$, the left/right determination portion 14 determines that the subject image is turned sideways on the original image P0 so that the upper portion is on the left side of the image.

In this manner, the left/right determination portion 14 compares the variation of pixel values in the right area of the left/right determination image generated by extracting the contour of the image that appears in the original image P0 which is determined to be turned sideways by the sideways determination portion 13 and the variation of pixel values in the left area thereof, and determines that the area on the side with larger variance corresponds to the upper portion of the subject image.

The determination result of the left/right determination portion 14 is sent to the image rotation portion 16. The image rotation portion 16 rotates the original image P0 so that the upper portion of the subject image faces the upper side of the image according to the determination result. Thus, the image rotation portion 16 rotates the original image P0 so that the upper portion of the subject image faces the upper side of the original image P0 according to the determination result of the left-right determination portion.

Figure 21:
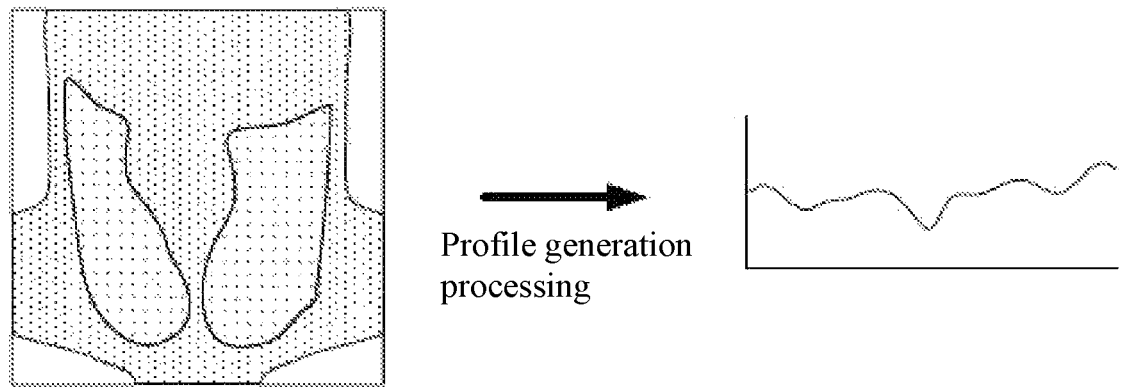
FIG. 21 is a schematic diagram explaining the problem of the profile according to Example 1.

By the way, even if the sideways determination portion 13 does not detect the sideways turning of the subject image, the orientation of the subject image is not necessarily suitable for diagnosis. FIG. 21 explains this situation. FIG. 21 shows an original image P0 in which the subject image is turned upside-down, and shows an image in which the subject image shown on the left side of FIG. 8 is oriented oppositely. The profile generated by the profile generation portion 11 based on the original image P0 shown in FIG. 21 is the similar to the profile on the subject image shown on the left side of FIG. 8. In the sideways determination portion 13, it is difficult to determine whether or not the subject image on the original image P0 is upside-down.

For this reason, the apparatus according to the present invention is provided with a configuration for determining whether the upper side of the subject image faces upwards of the image or the upper side of the subject image faces downwards of the image. This determination is performed by the up/down determination portion 15.

<Operation of Up/Down Determination Portion 15>

Figure 22:
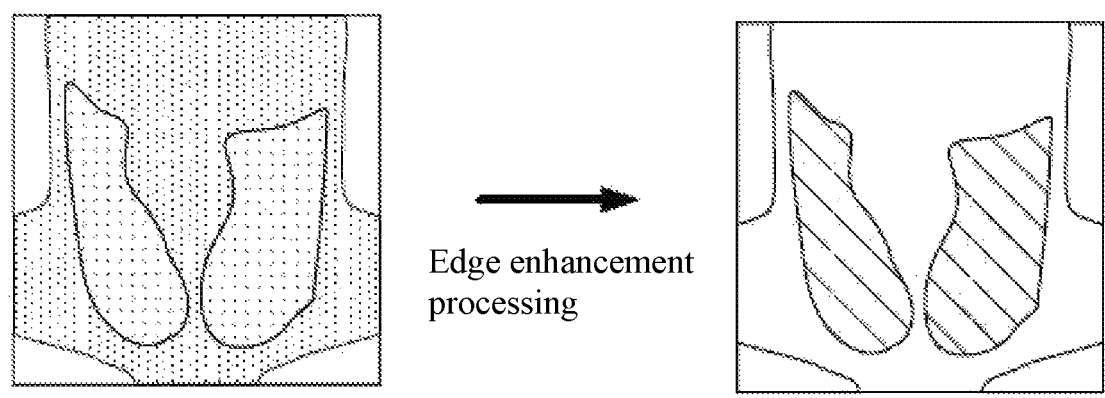
FIG. 22 is a schematic diagram explaining left/right determination processing according to Example 1.

To the up/down determination portion 15, the determination result of the sideways determination portion 13 is sent. When it is determined that the original image P0 includes a subject image appearing vertically, as shown in FIG. 22, the up/down determination portion 15 initially performs edge enhancement processing on the original image P0 to generate an edge enhanced image. The edge enhancement processing is performed by applying a filter, such as, e.g., a Laplacian filter, to the original image P0. The edge enhanced image generated at this time will be referred to as an up/down determination image in order to distinguish from the image depicted in FIG. 10.

The up/down determination portion 15 sets two areas on the up/down determination image, i.e., an upper area which corresponds to the upper half of the image and a lower area which corresponds to the lower half of the image. That is, the upper area and the lower area are set by horizontally dividing the up/down determination image into two equal parts. Then, the up/down determination portion 15 calculates the standard deviation $\sigma(a)$ of pixel values of the pixels belonging to the upper area and the standard deviation $\sigma(b)$ of pixel values of the pixels belonging to the lower area.

Figure 23:
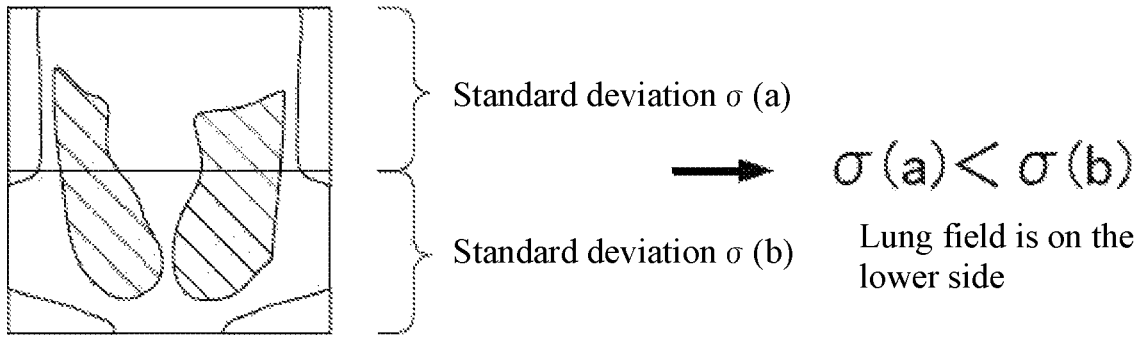
FIG. 23 is a schematic diagram explaining the left/right determination processing according to Example 1.

FIG. 23 shows an up/down determination image according to the original image P0 in which the subject image is turned upside-down so that the upper portion is positioned on the lower side of the image appears. The standard deviation σ(b) calculated from this image is larger than the standard deviation σ(a). This is because that the subject's lung field is shifted to the lower side of the image. Since the majority of the lung field should be shifted toward the upper portion of the subject image, the lower area of the original image P0 corresponds to the upper portion of the subject image. Based on this principle, when the standard deviation σ(b) is larger than the standard deviation σ(a), the up/down determination portion 15 determines that the subject image is turned upside-down on the original image P0 so that the upper portion is on the lower side of the image.

Figure 24:
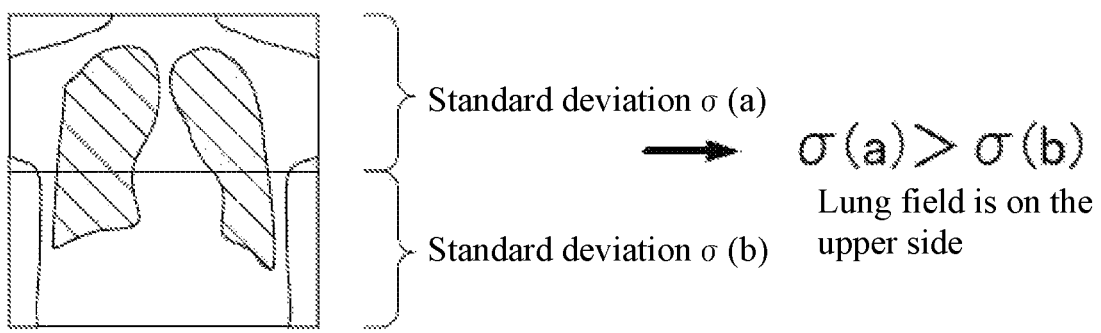
FIG. 24 is a schematic diagram explaining left/right determination processing according to Example 1.
Figure 25:
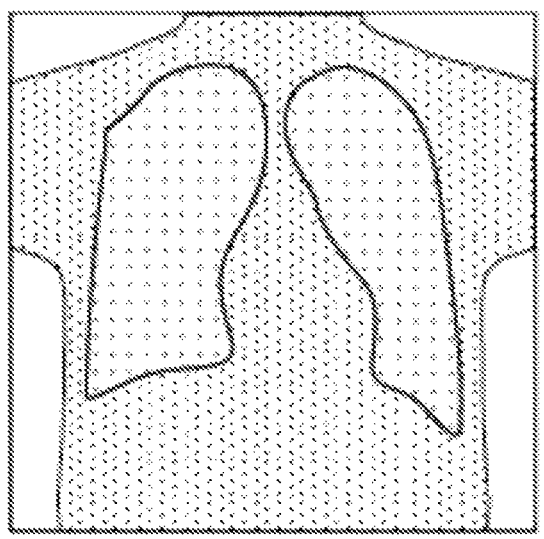
FIG. 25 is a schematic diagram explaining image processing of a conventional configuration.
Figure 26:
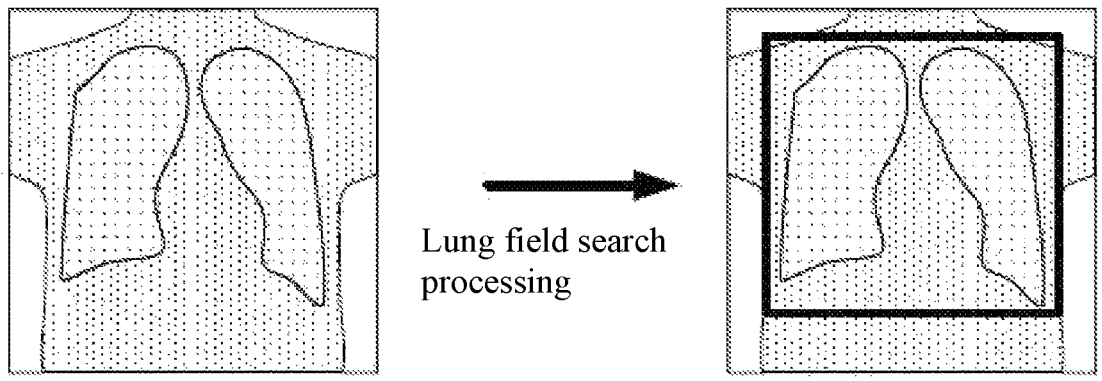
FIG. 26 is a schematic diagram explaining image processing of a conventional configuration.
Figure 27:
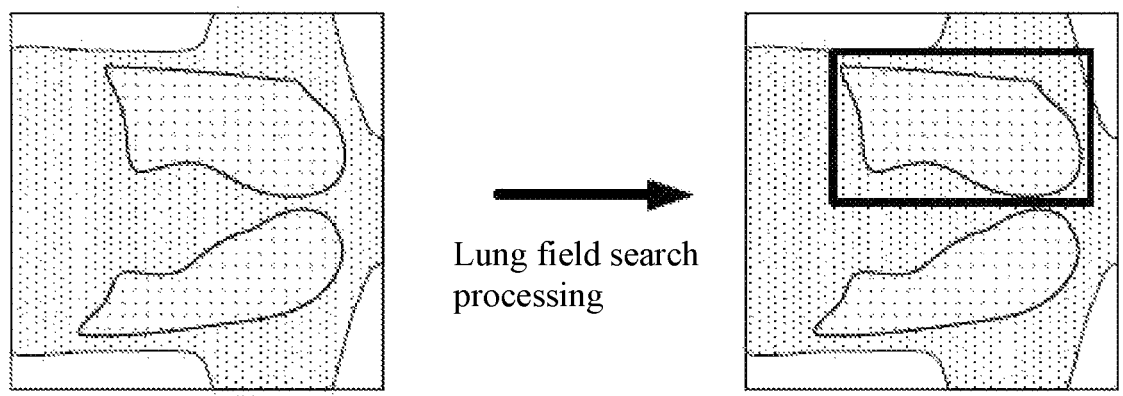
FIG. 27 is a schematic diagram explaining image processing of a conventional configuration.

FIG. 24 shows an up/down determination image according to the original image P0 in which the subject image appears so that the upper portion is positioned on the upper side of the image appears. The standard deviation σ(a) calculated from this image is larger than the standard deviation σ(b). This is because that the subject's lung field is shifted to the upper side of the image. Since the majority of the lung field should be shifted toward the upper portion of the subject image, the upper area of the original image P0 corresponds to the upper portion of the subject image. Based on this principle, when the standard deviation σ(a) is larger than the standard deviation σ(b), the up/down determination portion 15 determines that the subject image appears on the original image P0 so that the upper portion is on the upper side of the image.

In this manner, the up/down determination portion 15 compares the variation of pixel values in the upper area of the up/down determination image generated by extracting the contour of the image that appears in the original image P0 which is determined by the sideways determination portion 13 so that the subject appears vertically in the original image P0 and the variation of pixel values in the lower area thereof, and determines that the area on the side with larger variance corresponds to the upper portion of the subject image.

The determination result of the up/down determination portion 15 is sent to the image rotation portion 16. The image rotation portion 16 rotates the original image P0 in which the subject image is turned upside-down so that the upper portion is at the lower side of the image appears by 180°. Note that the image rotation portion 16 does not rotate the original image P0 in which the subject image appears on the original image P0 so that the upper portion is at the upper side of the image. That is, the image rotation portion 16 rotates the original image P0 so that the upper portion of the subject image positioned at the lower side of the original image P0 faces upward of the original image P0.

To the lung field search processing portion 17, the original image P0 is sent from the image rotation portion 16. Since this original image P0 is an image after the rotation processing, the subject image appears so that the upper portion is at the upper side of the image. The lung field search processing portion 17 searches a lung field from the original image P0. The lung field search method at this time is based on the assumption that the subject image appears so that the upper side of the subject image is at the upper side of the original image P0. That is, the lung field search processing portion 17 operates assuming that the lung field is located below the neck portion by searching the neck portion of the subject at the upper portion of the original image P0, operates assuming that the edge of the left lung is positioned at the left end of the original image P0 and the edge of the right lung is positioned at the right end of the original image P0, or operates assuming that the end portion of the left lung or the right lung is positioned below the original image P0.

Since the subject image appears in the original image P0 so that the upper portion is at the upper side of the image, the lung field search processing portion 17 can reliably search the lung field without false recognition. The lung field search processing portion 17 searches the lung field which appears in the original image P0 after the rotation processing. The lung field search processing portion 17 searches the lung field for the original image P0 which is determined that the subject image appears vertically in the original image P0 by the sideways determination portion 13 and performs the lung field search.

To the luminance adjustment portion 18, the data indicating where the lung field area searched by the lung field search processing portion 17 corresponds in the original image P0 is sent. The luminance adjustment portion 18 performs a color tone correction on the lung field area to improve the visibility of the lung field. The luminance adjustment portion 18 may generate a trimmed image by performing trimming processing in which the lung field area after the color tone correction is extracted and make it independent. Through such operations, operations of the apparatus of the present invention are completed.

As described above, according to the present invention, it is possible to provide an image processing apparatus 1 capable of assuredly finding a lung field that appears in an image even if a subject image appears in the original image P0 in a rotated manner and assuredly performing a contrast adjustment with excellent visibility for the lung field. That is, the image processing apparatus is provided with a sideways determination means configured to determine that the subject image is turned sideways in the original image P0 when a minimum point P of a profile generated by summing or averaging pixel values belonging to each pixel column of the original image P0 for each pixel column is away from the center position of the subject image. The original image P0 determined as being turned sideways by the sideways determination portion 13 is rotated by the image rotation portion 16 and used for searching of the lung field. Therefore, according to the present invention, even if the subject image appears in a rotated manner in the original image P0, the lung field search can be performed with the subject image corrected to the correct orientation, so that a contrast adjustment with excellent visibility can be assuredly performed for the lung field.

The present invention is not limited to the aforementioned embodiments, but can be modified as follows.

(1) The present invention can also be applied to the radiation imaging apparatus on which the above-described image processing apparatus 1 is mounted.

(2) The image processing apparatus 1 according to the present invention can also be realized by executing the following processing. That is, software (program) for realizing the functions of the above-described embodiments is supplied to a system or an apparatus via a network or various storage media, and a computer (or CPU, MPU, etc.) of the system or apparatus reads the program to execute processing.

(3) According to the above-described Example, the profile generation portion 11 is configured to generate a profile by calculating the average value for each pixel column constituting the original image P0. However, the present invention is limited to this configuration. The profile generation portion 11 may repeat the operation of summing pixel values of pixels belonging to a pixel column and generate the profile by arranging the calculated sum according to the position of the pixel column.

(4) According to the above-described Example, the left/right determination portion 14 and the up/down determination portion 15 calculate the deviation of pixel values by calculating the standard deviation, but the present invention is not limited to this configuration. The left/right determination portion 14 and the up/down determination portion 15 may operate by computing indexes indicating variations other than a standard deviation.

(5) According to the above-described Example, the left/right determination portion 14 vertically divides the determined left/right description image into two equal parts, but the present invention is not limited to this configuration. Each area may be set so that even if the right area and the left area are combined, the combined area does not become the entire area of the determined left/right image. Further, the width of the right area and the width of the left area may be different.

(6) According to the above-described Example, the up/down determination portion 15 vertically divides the determined up/down image into two equal parts, but the present invention is not limited to this configuration. Each area may be set so that even if the upper area and the lower area are combined, the combined area does not become the entire area of the determined up/down image. Further, the width of the upper area and the width of the lower area may be different.

DESCRIPTION OF REFERENCE SYMBOLS 11 profile generation portion (profile generation means)
12 center position calculation portion (center position calculation means)
13 sideways determination portion (sideways determination means)
16 image rotation portion (image rotation means)
17 lung field search processing portion (lung field search processing means)

The invention claimed is:

1. An image processing apparatus configured to apply a luminance adjustment to a lung field corresponding portion of a radiation image in which a subject image appears, the image processing apparatus comprising:
a processor, configured to:
generate a profile by summing or averaging pixel values belonging to each pixel column of the radiation image for each pixel column;
calculate a center position which is a position of a center of the subject image which appears in the radiation image;
determine that the subject image is turned sideways in the radiation image when a minimum position which is a position where a value of a profile is minimum is away from the center position of the subject image and determine that the subject image appears vertically in the radiation image when the minimum position of the profile is in a vicinity of the center position; and
search the lung field which appears in the radiation image based on a determination result.

2. The image processing apparatus as recited in claim 1, further comprising:
the processor configured to:
perform rotation processing for rotating the radiation image with respect to the radiation image determined as being turned sideways by the sideways determination,
wherein the processor performs searching of the lung field for the radiation image after the rotation processing.

3. The image processing apparatus as recited in claim 1, wherein
the processor performs searching of the lung field for the radiation image determined by the sideways determination that the subject image appears vertically in the radiation image.

4. The image processing apparatus as recited in claim 2, further comprising:
processor configured to:
determine that an area on a side with larger variations corresponds to an upper portion of the subject image by comparing a variation in pixel values in an area on a right side of a contour extracted image and a variation in pixel values in an area on a left side of the contour extracted image, the contour extracted image being generated by extracting a contour of the image appearing in the radiation image determined as being turned sideways by the sideways determination,
wherein the processor rotates the radiation image so that the upper portion of the subject image faces an upper side of the radiation image depending on a determination result of the left/right determination.

5. The image processing apparatus as recited in claim 2, further comprising:
the processor configured to:
determine that an area on a side with larger variations corresponds to an upper portion of the subject image by comparing a variation in pixel values in an area on an upper side of a contour extracted image and a variation in pixel values in an area on a lower side of the contour extracted image, the contour extracted image being generated by extracting a contour of the image appearing in the radiation image determined as appearing vertically in the radiation image by the sideways determination;
wherein the processor rotates the radiation image so that the upper portion of the subject image positioned below the radiation image faces the upper side of the radiation image.

6. A program in non-transitory storage media causing a computer to function within the image processing apparatus as recited in claim 1.

7. A radiation imaging apparatus equipped with the image processing apparatus as recited in claim 1.

* * * * *